United States Patent [19]

Butler et al.

[11] Patent Number: 4,677,112

[45] Date of Patent: Jun. 30, 1987

[54] 1,2,3,4-TETRAHYDRO-2-OXO-8-QUINOLINEACETIC AND -PROPANOIC ACIDS AND DERIVATIVES AS COGNITION ACTIVATORS

[75] Inventors: Donald E. Butler; Michael R. Pavia; Fred M. Hershenson, all of Ann Arbor, Mich.

[73] Assignee: Warner-Lambert Company, Morris Plains, N.J.

[21] Appl. No.: 800,853

[22] Filed: Nov. 22, 1985

Related U.S. Application Data

[62] Division of Ser. No. 576,288, Feb. 2, 1984, Pat. No. 4,582,909.

[51] Int. Cl.$^4$ .................... A61K 31/47; C07D 215/22
[52] U.S. Cl. .................................. 514/312; 546/158
[58] Field of Search .................. 546/158; 514/312

[56] References Cited

U.S. PATENT DOCUMENTS 4,530,929  7/1985  Butler et al. ...................... 514/295
4,578,381  3/1986  Uchida et al. ...................... 514/233
4,579,854  4/1986  Iwakuma et al. .................... 514/312
4,582,909  4/1986  Butler et al. ....................... 548/486

OTHER PUBLICATIONS

Adams et al., Chemical Abstracts, vol. 51, 17919a (1957).
Munoz et al., Chemical Abstracts, vol. 56, 7275c (1962).
Stefanovica et al., Chemical Abstracts, vol. 59, 9977a (1963).

*Primary Examiner*—Donald G. Daus
*Assistant Examiner*—Diana G. Rivers
*Attorney, Agent, or Firm*—Jerry F. Janssen

[57] ABSTRACT

Benzobicyclic lactam acids having a fused aromatic carbocyclic and a saturated lactam ring of five- or six-members, their salts, esters, and amides, are useful in the treatment of senility and for reversing amnesia. Pharmaceutical compositions including these compounds, a method of preparing the compounds, and a method of treating senility and reversing amnesia area also disclosed.

16 Claims, No Drawings

1,2,3,4-TETRAHYDRO-2-OXO-8-QUINOLINEACETIC AND -PROPANOIC ACIDS AND DERIVATIVES AS COGNITION ACTIVATORS

CROSS-REFERENCE TO RELATED APPLICATIONS

This application is a divisional of copending application Ser. No. 576,288, filed Feb. 2, 1984, now U.S. Pat. No. 4,582,909 issued Apr. 15, 1986. This application discloses and claims subject matter which relates to subject matter disclosed in copending application Ser. No. 576,242, now U.S. Pat. No. 4,530,929 issued July 23, 1985.

BACKGROUND OF THE INVENTION

The present invention relates to compounds and pharmaceutical compositions useful in the treatment of senility and the reversal of amnesia. More particularly, it is concerned with certain benzobicyclic lactam acids and their derivatives, with a method of preparing such compounds, pharmaceutical compositions including these compounds, and a method of treating senility and reversing amnesia.

SUMMARY AND DETAILED DESCRIPTION

In its broadest aspect, the present invention relates to compounds having the structural formula I:

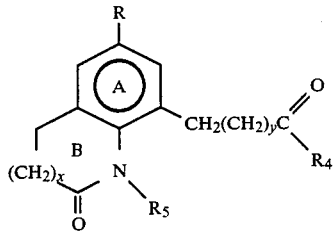

wherein x, and y are independently zero or one; R is hydrogen; halogen; hydroxyl; —$OR_1$ where $R_1$ is alkyl of from one to six carbon atoms, phenyl, or phenylmethyl; or —$NR_2R_3$ where $R_2$ and $R_3$ are independently alkyl of from one to six carbon atoms; $R_4$ is selected from —OH, together with the pharmaceutically acceptable metal, ammonium and amine addition salts thereof; —$OR_1$, where $R_1$ is previously defined;

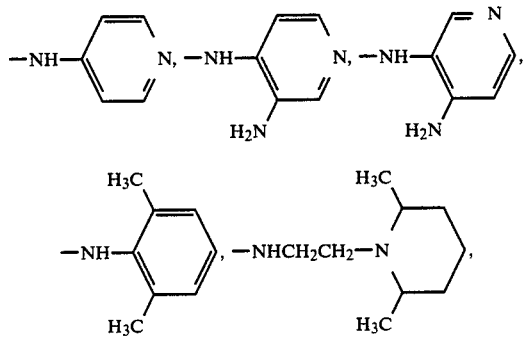

—$NHCH_2CH_2N[CH(CH_3)_2]_2$; and —$NR_6R_7$ where $R_6$ and $R_7$ are independently hydrogen or alkyl of from one to six carbon atoms, and the pharmaceutically acceptable acid addition salts thereof; and $R_5$ is hydrogen or

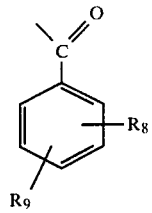

where $R_8$ and $R_9$ are independently hydrogen; halogen; hydroxyl; —$OR_1$ where $R_1$ is as defined above; $NR_{10}R_{11}$ where $R_{10}$ and $R_{11}$ are independently hydrogen, alkyl of from one to six carbon atoms, or when taken together and attached to adjacent carbon atoms are —$OCH_2O$—.

Compounds of the present invention, represented by structure I, comprise a class of structurally related bicyclic fused-ring compounds containing both a lactam ring and a substituted or unsubstituted aromatic ring having an attached side-chain acetic or propanoic acid group including particular salt, ester, or amide derivatives thereof, and in which the lactam ring nitrogen atom is optionally substituted with benzoyl or substituted-benzoyl.

Although the compounds contemplated by the present invention are structurally related, their nomenclature is somewhat complex. The names of the compounds are based in part on the names of the corresponding unsaturated nitrogen-containing fused-ring systems.

The aromatic carbocyclic ring (A as indicated in the structure above) may either be unsubstituted or is mono-substituted, preferably at the position indicated in structure I, with halogen, hydroxyl, alkoxyl of from one to six carbon atoms, phenoxy, phenylmethoxy, or dialkylamino in which the alkyl groups contain from one to six carbon atoms.

Also contemplated as falling within the scope of this invention are compounds in which the acetic or propanoic acid side-chain attached to the aromatic carbocyclic ring is converted to pharmaceutically acceptable salts, including the salts with acceptable metal or amine cations, or is converted to esters, preferably esters derived from alcohols containing from one to six carbon atoms, phenol, and phenylmethanol, or is converted to an amide function by reaction with an amine by standard chemical activation methods. Preferred amines for this purpose are selected from the mono- and dialkylamines containing from one to six carbon atoms, particularly methylamine, ethylamine, dimethylamine, diethylamine, and from the group consisting of N,N-diisopropylaminoethylamine, 2,6-dimethylaniline, cis- or trans-2,6-dimethylpiperidinylethylamine, 4-aminopyridine, 3,4-diaminopyridine.

The invention also contemplates salts of those compounds falling within generic structure I in which the group R, $R_4$, or $R_5$ contain a nitrogen atom of sufficient basicity to form acid addition salts with pharmaceutically acceptable acid anions. Included in such groups are R=dialkylamine, and $R_4$=3,4-diaminopyridinyl, 2,6-dimethylpiperidinylethylamino, and $R_5$=alkylaminobenzoyl, dialkylaminobenzoyl, bis(alkylamino)benzoyl, and bis(dialkylamino)benzoyl.

Non-toxic, pharmaceutically acceptable acid addition salts of the foregoing classes of compounds falling within the scope of this invention are formed by the reaction of the free base with any number of inorganic and organic acids including, but not necessarily limited to hydrochloric, hydrobromic, hydriodic, sulfuric, nitric, phosphoric, acetic, benzoic, citric, maleic, malic, tartaric, succinic, gluconic, ascorbic, sulfamic, oxalic, pamoic, methanesulfonic, benzenesulfonic, and related acids and mixtures thereof.

The free base forms and the salts, both anionic cationic salts, of compounds of this invention may differ somewhat in their physical properties such as solubility in polar solvents, etc., but for the purposes of this invention are considered as equivalent.

The invention further contemplates compounds in which a substituted or unsubstituted benzoyl group is attached to the nitrogen atom of the lactam ring. The benzoyl group may be unsubstituted, or substituted with one or two groups. The benzoyl group, if substituted, is preferably substituted with hydroxyl; alkoxyl of from one to six carbon atoms, particularly methoxy, ethoxy; phenoxy, and phenylmethoxy; halogen, particularly, chlorine or fluorine; amino; monoalkylamino or dialkylamino of from one to six carbon atoms, particularly methyl or dimethylamine: or methylenedioxy.

Stereoisomerism may be introduced into compounds of the present invention by the presence of asymmetric carbon atoms in alkyl groups forming the whole or part of substituent groups R, $R_4$, or $R_5$ as defined above. The present invention contemplates all possible stereoisomers encompassed generically by structural formula I given above. The terms "stereoisomers" and "stereoisomerism" as used throughout this specification and the appended claims are to be given the meaning usually ascribed to them by practitioners of the organic chemical arts, and specifically as defined by Eliel in "Stereochemistry of Carbon Compounds," pp. 1–6, McGraw-Hill, New York, 1962.

The present invention contemplates all possible ring-size variants, geometrical isomers, and optical isomers of the compounds depicted generically by structural formula I given above.

The term "alkyl of from one to six carbon atoms" as used herein contemplates branched and unbranched hydrocarbon groupings containing one to six carbon atoms as, for example, methyl, ethyl, n- and isopropyl, n-, sec-, iso-, and tert-butyl, n-, iso-, sec-, and neopentyl, n-, sec-, and iso-hexyl, etc.

Compounds falling within the scope of the present invention include, but are not necessarily limited to, the following examples.

2,3-Dihydro-2-oxo-1H-indole-7-acetic acid and the pharmaceutically acceptable salts thereof.
2,3-Dihydro-1-(3-methoxybenzoyl)-2-oxo-1H-indole-7-acetic acid and the pharmaceutically acceptable salts thereof.
2,3-Dihydro-1-(4-methoxybenzoyl)-2-oxo-1H-indole-7-acetic acid and the pharmaceutically acceptable salts thereof.
2,3-Dihydro-1-(4-methoxybenzoyl)-2-oxo-1H-indole-7-propanoic acid and the pharmaceutically acceptable salts thereof.
1-[4-(Dimethylamino)benzoyl]-1,2,3,4-tetrahydro-2-oxo-8-quinolineacetic acid and the pharmaceutically acceptable salts thereof.
1-[4-Methoxy-3-(phenylmethoxy)benzoyl]-1,2,3,4-tetrahydro-2-oxo-8-quinolinepropanoic acid and the pharmaceutically acceptable salts thereof.
1-(1,3-Benzodioxol-5-ylcarbonyl)-1,2,3,4-tetrahydro-2-oxo-8-quinolinepropanoic acid and the pharmaceutically acceptable salts thereof.
2,3-Dihydro-1-(4-hydroxy-3-methylbenzoyl)-2-oxo-1H-indole-7-acetic acid and the pharmaceutically acceptable salts thereof.
2,3-Dihydro-2-oxo-1H-indole-7-propanoic acid, and the pharmaceutically acceptable salts thereof.
1,2,3,4-Tetrahydro-2-oxo-8-quinolineacetic acid, and the pharmaceutically acceptable salts thereof.
1-(4-Methoxybenzoyl)-1,2,3,4-tetrahydro-2-oxo-8-quinolineacetic acid and the pharmaceutically acceptable salts thereof.
1-Benzoyl-2,3-dihydro-2-oxo-1H-indole-7-acetic acid and the pharmaceutically acceptable salts thereof.
2,3-Dihydro-1-(3-hydroxy-4-methoxybenzoyl)-2-oxo-1H-indole-7-acetic acid and the pharmaceutically acceptable salts thereof.
2,3-Dihydro-2-oxo-1H-indole-7-acetic acid methyl ester.
2,3-Dihydro-2-oxo-1H-indole-7-acetic acid phenylmethyl ester.
2,3-Dihydro-2-oxo-1H-indole-7-propanoic acid methyl ester.
2,3-Dihydro-2-oxo-1H-indole-7-propanoic acid phenylmethyl ester.
1,2,3,4-Tetrahydro-2-oxo-8-quinolineactic acid ethyl ester.
1,2,3,4-Tetrahydro-2-oxo-8-quinolineactic acid phenylmethyl ester.
1,2,3,4-Tetrahydro-2-oxo-8-quinolinepropanoic acid ethyl ester.
1,2,3,4-Tetrahydro-2-oxo-3-quinolinepropanoic acid phenylmethyl ester.
1-(2-Chlorobenzoyl)-5-fluoro-2,3-dihydro-2-oxo-1H-indole-7-propanoic acid methyl ester.
1-(2-Fluorobenzoyl)-6-methoxy-1,2,3,4-tetrahydro-2-oxo-8-quinolineacetic acid phenyl ester.
1-(2-Methoxybenzoyl)-1,2,3,4-tetrahydro-2-oxo-6-phenoxy-8-quinolinepropanoic acid and the pharmal5 ceutically acceptable salts thereof.
1-(2-Methoxybenzoyl)-1,2,3,4-tetrahydro-2-oxo-6-phenoxy-8-quinolinepropanoic acid phenylmethyl ester.
2,3-Dihydro-2-oxo-1e,uns/H/ -indole-7-acetamide.
2,3-Dihydro-2-oxo-N-4-pyridinyl-1H-indole-7- acetamide.
N-[2-[bis(1-methylethyl)amino]ethyl]-2,3-dihydro-2-oxo-1H-indole-7-acetamide.

Also contemplated within the scope of the present invention are the compounds [(2,3-dihydro-2-oxo-1H-indole-7-yl)methyl]-propandioic acid and its dimethyl ester which are particularly useful as intermediates in the preparation of compounds of formula I where x is zero and y is one.

The compounds of the present invention (structure I where $R_4$ is hydroxyl) form salts with pharmaceutically acceptable metal or amine cations derived from organic and inorganic bases. The term "pharmaceutically acceptable metal cation" contemplates positively charged metal ions such as those derived from sodium, potassium, calcium, magnesium, aluminum, iron, zinc, and the like.

The term "pharmaceutically acceptable amine cation" contemplates the positively charged ions derived from ammonia and organic nitrogenous bases strong enough to form such cations. Bases useful for the formation of pharmaceutically acceptable non-toxic acid addition salts of compounds containing a carboxyl acid function form a class whose limits are readily understood by those skilled in the art.

Merely for illustration, this class of amines can be said to comprise, in cationic form, those of the formula:

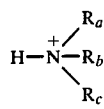

wherein $R_a$, $R_b$, and $R_c$ independently are hydrogen, alkyl of from one to six carbon atoms, cycloalkyl of from about three to six carbon atoms, aryl, aralkyl of from about seven to about ten carbon atoms, hydroxyalkyl of from two to four carbon atoms, or monoarylhydroxyalkyl of from about eight to about fifteen carbon atoms. Further, when taken together with the nitrogen atom to which they are attached, any two of $R_a$, $R_b$, and $R_c$ may form part of a five- or six-membered nitrogen-containing heterocyclic aromatic or non-aromatic ring containing carbon or oxygen, said nitrogen-containing heterocyclic rings being unsubstituted, monosubstituted, or disubstituted with alkyl groups of from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and isopropyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like.

The ammonium, amine, or metal salts are prepared by reaction of the appropriate acetic or propanoic acid compound of this invention with an equivalent amount of an organic amine base or an inorganic base such as ammonium hydroxide, sodium hydroxide, potassium hydroxide, sodium carbonate, calcium carbonate, sodium bicarbonate, and the like in an appropriate solvent such as water or an aqueous alcohol, followed by removal of the solvent under reduced pressure.

The free acid form of the compound may be regenerated from the salts, if desired, by contacting the salt with a dilute aqueous solution of an acid such as hydrochloric.

The compounds of formula I where both x and y are zero are prepared by the general method detailed in Reaction Scheme 1.

Reaction Scheme I

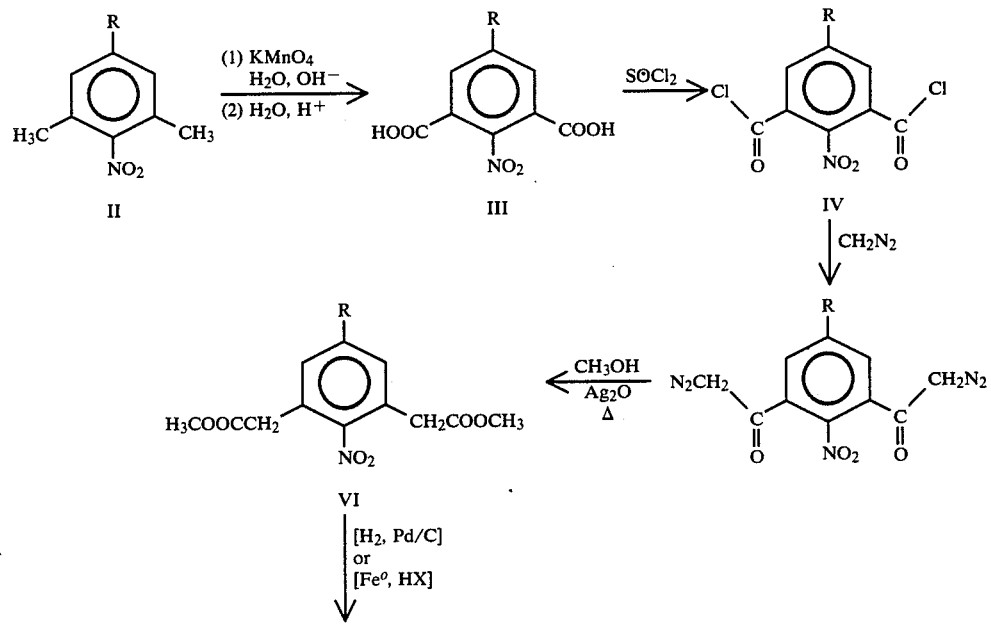

-continued
Reaction Scheme 1

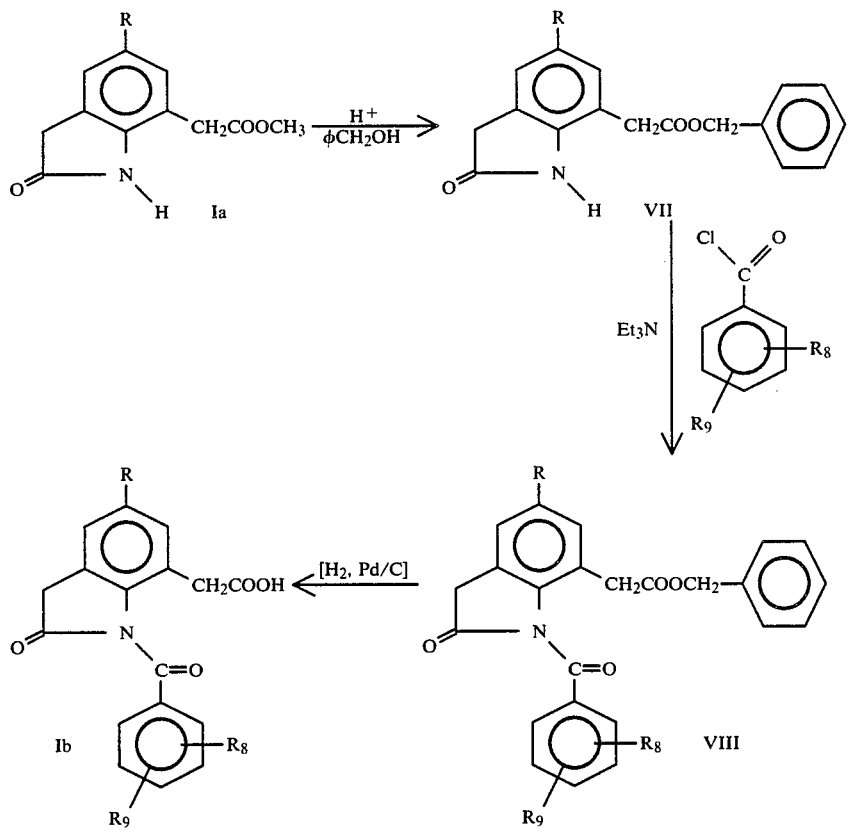

Appropriately substituted 2,6-dimethyl-1-nitrobenzenes (II) are oxidized to the corresponding 2-nitro-1,3-benzenedicarboxylic acids (III) as described by E. Notting and C. Gachot, Chem. Ber., 39:73-75 (1906). The diacids (III) are converted to 2-nitrobenzenedicarbonyl chlorides (IV) by reaction with, for example, thionyl chloride in 1,1,2,2-tetrachloroethane.

The dicarbonyl chlorides (IV) are converted to 2-nitro-1,3-diazoacetylbenzenes (V) by reaction with, for example, diazomethane in diethyl ether. The diazoacetylbenzene compounds (V) are converted to the corresponding dimethyl esters (VI) by the well-known Arndt-Eistert synthesis (see, for example W. E. Bachmann and W. S. Struve, Organic Reactions, Volume I, 38 (1942). Reduction of the diesters (VI) with, for example, hydrogen over palladium/carbon catalyst cyclizes the diesters to produce compounds Ia in accordance with formula I where both x and y are zero and $R_4$ is methoxy. These compounds can be converted, if desired, to the free acids, to salts of the free acids, esters of other alcohols, or amides by conventional reactions well known to practitioners of the art.

The methyl esters, compounds Ia may be converted to the free acids by hydrolysis, and thence further to their salts by conventional techniques or, alternatively, compounds Ia may be transformed into the phenylmethyl esters VII by transesterification. The phenylmethyl esters may be reacted with a substituted or unsubstituted benzoyl chloride compound in, for example, toluene in the presence of a catalyst such as triethylamine, to produce the benzoylated derivatives compounds VIII. Hydrogenolysis of the compounds VIII yields the benzoylated free acid compounds Ib.

The compounds of formula I where x is zero and y is one, or vice versa, are prepared by the general methods detailed in Reaction Scheme 2.

Reaction Scheme 2

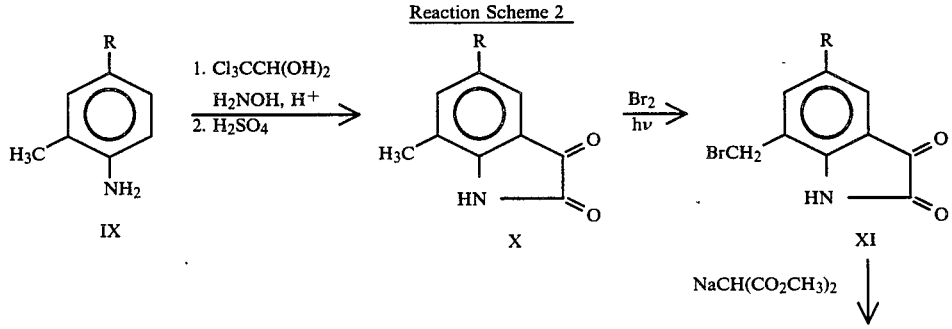

-continued
Reaction Scheme 2
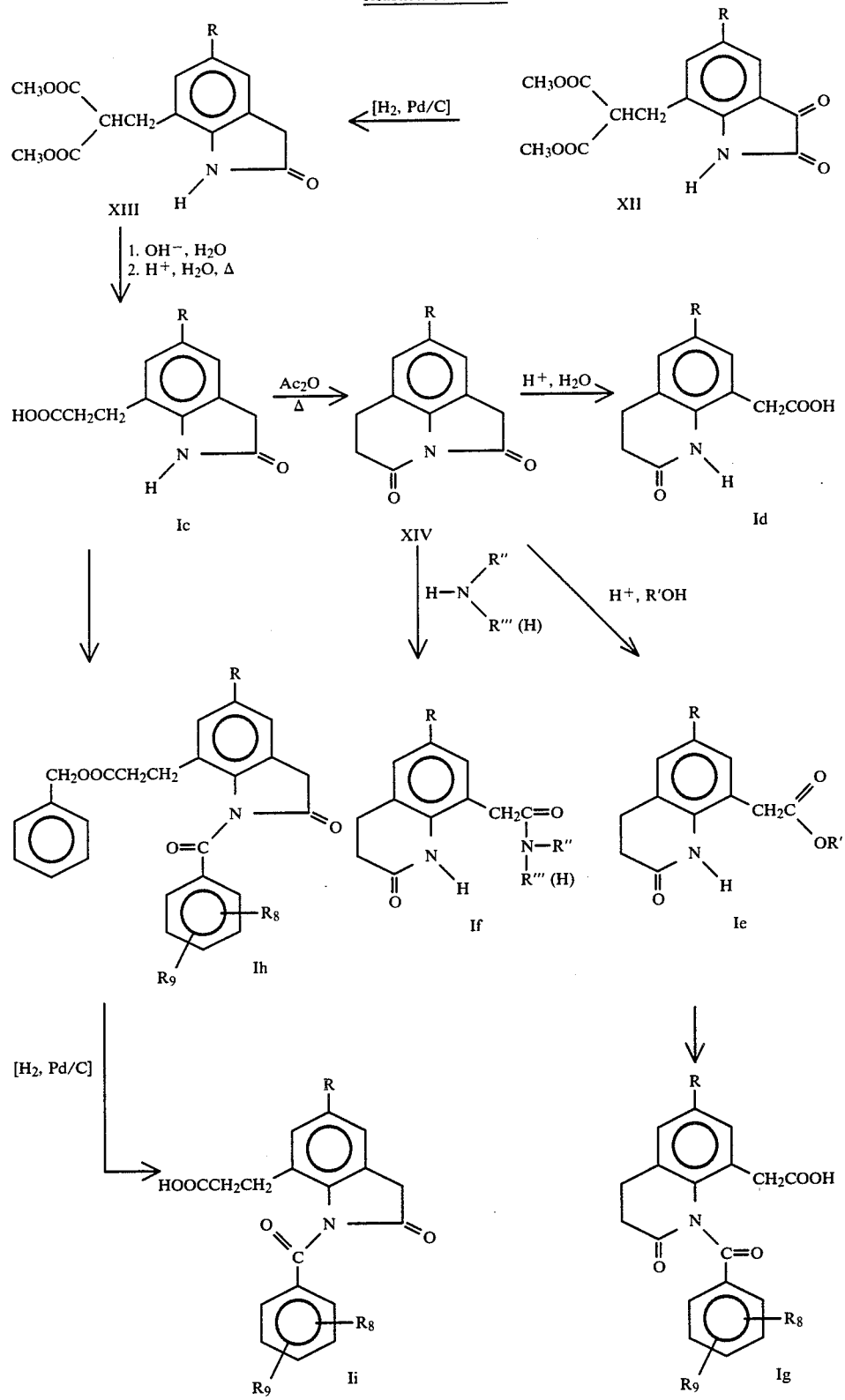
The known 4-substituted-2-methylanilines (IX) are converted to the corresponding 5-substituted-7-methylisatins (X) by the reaction described in A. Wahl et al., *Ann. Chim.*, 5:323 (1926). The 5-chloro-7-methylisatin [H. Pajouhesh et al., *J. Pharm. Sci.*, 72: 381–421 (1983)] and the 5-bromo-7-methylisatin [German Offenlegungschrift DR No. 2,925,175] are known compounds.

The methyl group of the isatins (X) is subsequently photocatalytically halogenated by reaction with, for example, bromine under ultraviolet light in an inert solvent such as dichloromethane containing a trace amount of water, to produce the 5-substituted-7-bromomethylisatins (XI).

Reaction of the 7-bromomethylisatins (XI) with the sodio derivative of malonic acid dimethyl ester in, for example, tetrahydrofuran at 0° C. produces the diesters (XII). Reduction of compounds XII with, for example, hydrogen over palladium/carbon catalyst yields compounds XIII. Saponification of the diesters, XIII, in dilute aqueous base, followed by acidification and heating, results in decarboxylation to produce the monocarboxylic acid compounds Ic where x is zero, y is one, and $R_4$ is —OH.

The compounds Ic may be further converted, if desired, to the tricyclic diones XIV by cyclization in acetic anhydride, and the resulting tricyclic dione compounds solvolyzed in dilute aqueous acid to yield the corresponding bicyclic lactam acids, Id, where x is one and y is zero, or solvolyzed in acidic alcohol to produce the bicyclic lactam esters Ie. Similarly, compound XIV may be ring-opened by reaction with the desired alkylamine or dialkylamine to produce the bicyclic lactam amides If.

This reaction sequence is particularly useful for the conversion of compounds in which the one of the lactam rings in the tricyclic compound is a five-membered ring and the other is six-membered to compounds of formula I in which x is one and y is zero. Solvolysis in alcoholic solution, catalyzed by a trace of acid, generally results in the formation of the product in which the smaller five-membered lactam ring is opened.

Compounds Ic or Id may be converted to their corresponding benzoylated or substituted-benzoylated ester derivatives by first converting the compounds to their esters by conventional means, and subsequently reacting the esters with benzoyl chloride or an appropriately substituted benzoyl chloride in, for example, toluene in the presence of an acid acceptor such as triethylamine.

Compounds Ie, where R' is phenylmethyl may be similarly substituted with benzoyl or substituted-benzoyl and subsequently converted to the free acids Ig by conventional hydrogenolysis reaction.

In an analogous manner, the acid compound Ic can be converted to its phenylmethyl ester by conventional means and subsequently substituted with benzoyl or substituted-benzoyl. The benzoylated phenylmethyl ester Ih can be converted to the benzoylated free acid Ii by hydrogenolysis.

The esters of free acid forms of the compounds are converted, if desired, to the corresponding salts, esters, or amides by conventional reactions known to those skilled in the art.

Compounds of formula I where both x and y are one are prepared by the general reaction sequence illustrated in Reaction Scheme 3.

Reaction Scheme 3

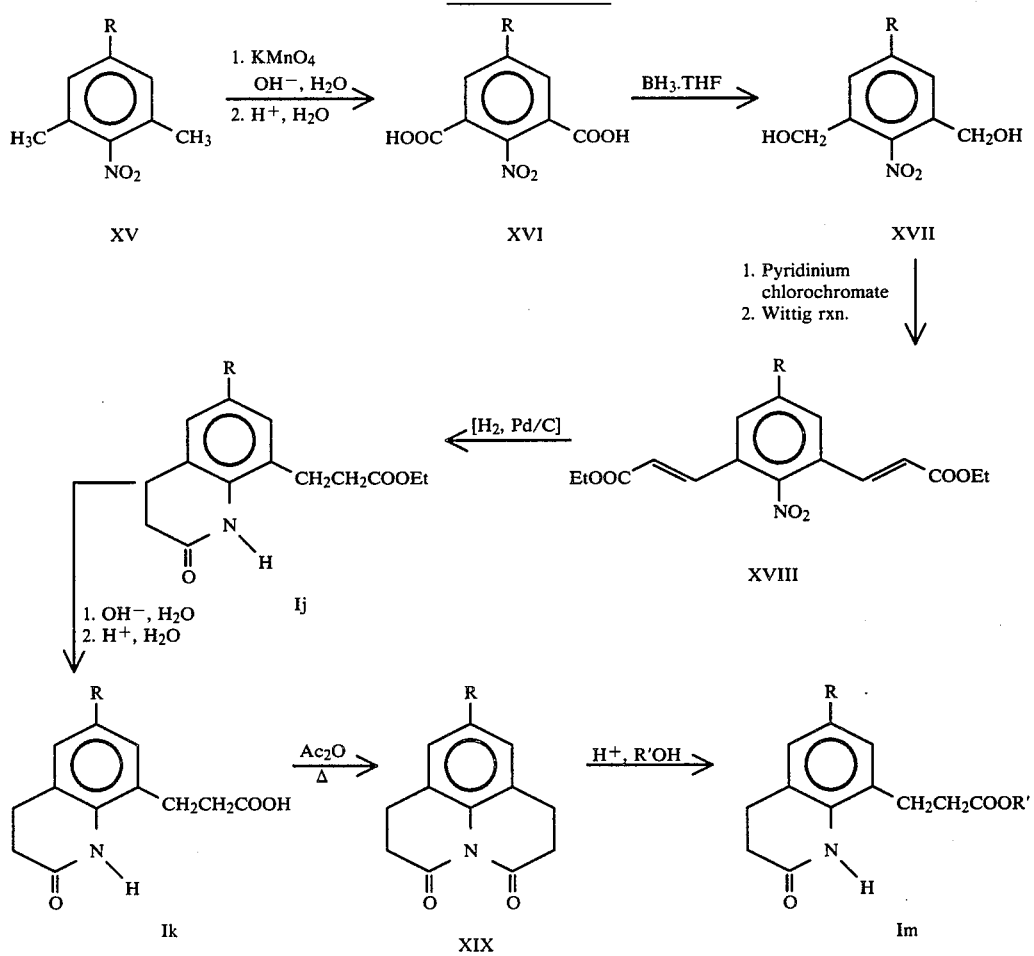

-continued
Reaction Scheme 3

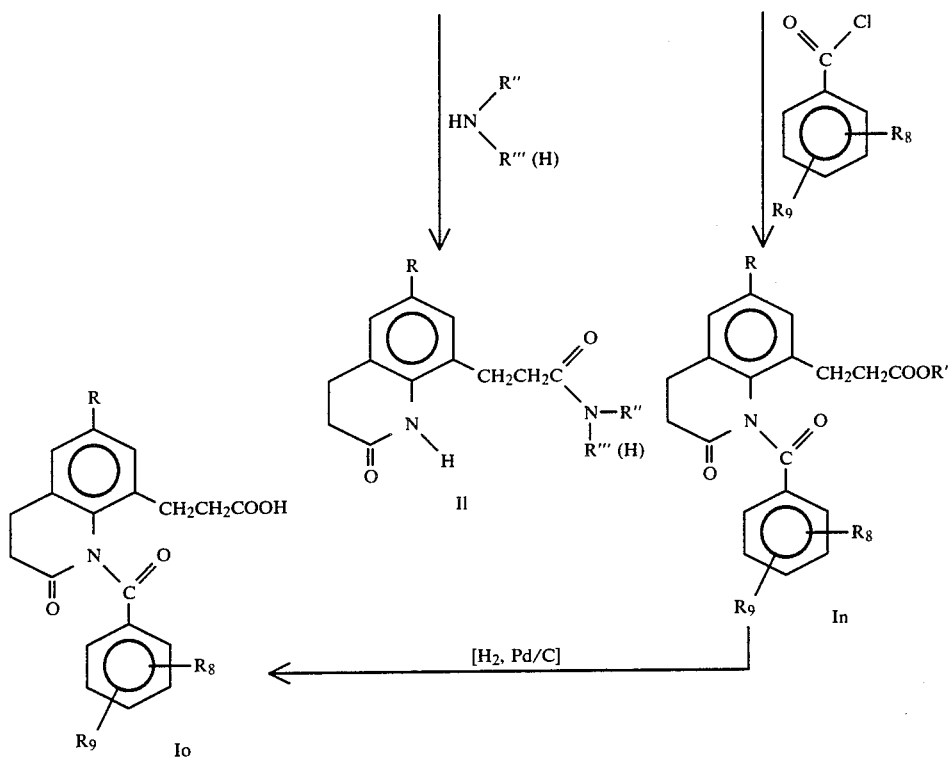

The 4-substituted-2,6-dimethylnitrobenzene compounds of formula XV, where R is hydrogen, fluorine, chlorine, or bromine, are oxidized, for example, by hot, aqueous, basic permanganate solution to the corresponding substituted isophthalic acid derivatives, XVI. These compounds are subsequently reduced, for example, by borane-tetrahydrofuran complex to the 4-substituted-2-6-bis(hydroxymethyl)-nitrobenzene compounds of forxula XVII. The hydroxymethyl groups are oxidized to the corresponding aldehyde groups by a mild oxidizing reagent such as pyridinium chlorochromate, and the aldehydes are converted to the diesters, XVIII, by the well-known Wittig Reaction (c.f. U. Schollkopf, Angew. Chem., 71:260(1959)).

In the specific instance where R is fluorine, the dialcohol compounds of formula XVII, or the diesters of formula XVIII may be conveniently converted to compounds where R is alkoxyl of from one to six carbon atoms, phenoxyl, phenylmethoxyl, or dialkylamino of from one to six carbon atoms by reaction with the appropriate alcohol or dialkylamine in dimethylformamide in the presence of potassium carbonate.

Catalytic reduction of the resulting compounds by hydrogen reduces both the nitro group and the carbon-carbon unsturation and cyclizes one lactam ring to produce compounds of formula Ij where x and y are both one, and $R_4$ is ethoxy. Saponification of the esters, Ij, in dilute base followed by acidification produces the acids, Ik, which may be used as such or converted, if desired, to pharmaceutically acceptable salts, esters, or amides by conventional techniques well known to practitioners of the art.

The acids, Ik, may be converted directly to the esters, Im, by conventional means, or cyclized to the tricyclic dione compounds XIX in acetic anhydride. In a preferred method of making the esters, Im, the resulting tricyclic dione compounds may be solvolyzed in the appropriate alcohols. Alternatively, compound XIX may be ring-opened by reaction with the appropriate alkylamine or dialkylamine to produce the bicyclic lactam amides Il.

The esters, Im, may be converted to their benzoylated derivatives, In, in a manner similar to that previously described. The benzoylated phenylmethyl esters may be converted to the benzoylated free acids, Io, by conventional hydrogenolysis.

The acids, Io, may be converted to desired salts, esters, or amides by conventional reactions well known to practitioners of organic chemical art.

Also in accordance with the present invention, pharmaceutical compositions may be produced by formulating compounds having structural formula I above in unit dosage form with a pharmaceutically acceptable carrier. Some examples of unit dosage forms are tablets, capsules, lozenges, and pills; as well as powders and aqueous and nonaqueous solutions and suspensions packaged in containers containing either one, or some larger number of dosage units and capable of being subdivided into individual doses by such means as measurement into a teaspoon or other standard container.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents, including other cognition activating agents such as 3-phenoxypyridine, and N-[N'N'-diisopropylaminoethyl] pyrrolidine-2-oxo-1-acetamide.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention contain from 0.1 to 250.0 mg, preferably from 1 to 75 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per day, preferably between about 25 mg to 750 mg per day, optionally administered in portions.

The compounds of the present invention are useful for treating senility or for reversing amnesia. The effectiveness of these compounds was evaluated by a test designed to show the ability of a given substance to reverse amnesia induced by electro-convulsive shock. The test is more fully described in U.S. Pat. No. 4,154,347, issued Mar. 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted employing compounds of the present invention appear in the Table I. The following criteria were used in interpreting the data: 40% or more amnesia reversal in the test animals=active, A; 25% to 39% amnesia reversal=borderline activity, C; 0% to 24% reversal of amnesia=inactive, N.

TABLE I

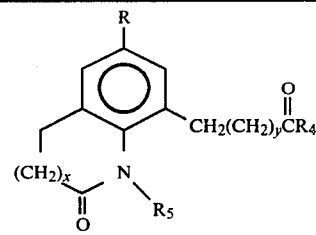

Percent Amnesia Reversal of Orally Administered Test Compounds (In Mice)

| Compound | x | y | R | $R_4$ | $R_5$ | Dose (mg/kg of Body Weight) | | |
|---|---|---|---|---|---|---|---|---|
| | | | | | | 100 | 10 | 1 |
| A | 0 | 0 | H | OH | H | 54(A) | 58(A) | 60(A) |
| B | 0 | 0 | H | $OCH_3$ | H | 92(A) | 33(C) | 42(A) |
| C | 1 | 1 | H | $OC_2H_5$ | H | 13(N) | 0(N) | 25(C) |

The following representative examples are provided to enable one skilled in the art to practice the present invention. These examples are merely illustrative of the preparation of compounds in accordance with the present invention and are not to be read as limiting the scope of the invention as defined by the appended claims.

EXAMPLE 1

Preparation of 2-nitro-1,3-benzenediacetic acid dimethyl ester 2,6-dimethyl-1-nitrobenzene is oxidized to 2-nitro-1,3-benzenedicarboxylic acid as described by E. Notting and C. Gachot; Chem. Ber., 39, 73–75 (1906) to yield 2-nitro-1,3-benzenedicarboxylic acid. A suspension of 2-nitro-1,3-benzenedicarboxylic acid (25 g, 0.118 mole) in 1,1,2,2-tetrachloroethane (100 ml) is treated with thionyl chloride (30 ml) and the mixture refluxed seven hours. The mixture is concentrated at reduced pressure and after recrystallization from n-heptane yields pure 2-nitro-1,3-benzenedicarbonyl chloride, mp 129°–131.5° C. A solution of diazomethane (4.2 g, 0.1 mole) in diethyl ether (500 ml) is cooled to 0° C. and 2-nitro-1,3-benzenedicarbonyl chloride (2.93 g, 0.0118 mole) is added in portions. The mixture is stirred 17 hours and concentrated at reduced pressure to yield 2-nitro-1,3-diazoacetylbenzene as a tan solid. The 2-nitro-1,3-diazoacetylbenzene is dissolved in methanol (250 ml) and the solution is added to freshly prepared silver oxide (synthesized by the reaction of 5 ml of a 10% silver nitrate solution with sodium hydroxide). The mixture is stirred at 0° C. for one hour and at 55°–60° C. for two hours. The solution is filtered and concentrated to yield crude 2-nitro-1,3-benzenediacetic acid dimethyl ester. Recrystallization from n-heptane yields pure 2-nitro-1,3-benzenediacetic acid dimethyl ester, mp 144°–145° C.

Preparation of 2,3-dihydro-2-oxo-1H-indole-7-acetic acid methyl ester

A solution of 2-nitro-1,3-benzenediacetic acid dimethyl ester (5.98 g, 0.022 mole) in tetrahydrofuran and methanol (2:1, 100 ml) is treated with hydrogen gas in the presence of 20% Pd/C for 18 hours. The mixture is filtered and concentrated at reduced pressure to yield 2,3-dihydro-2-oxo-1H-indole-7-acetic acid methyl ester. Final purification is accomplished using flash chromatography on silica (elution with 1:19 methanol:dichloromethane) and results in pure 2,3-dihydro-2-oxo-1H-indole-7-acetic acid methyl ester, mp 156°–157° C.

EXAMPLE 2

Preparation of 2,3-dihydro-2-oxo-1H-indole-7-acetic acid

A solution of 2,3-dihydro-2-oxo-1H-indole-7-acetic acid methyl ester (2.05 g, 0.01 mole) in methanol (50 ml) is treated with 1N sodium hydroxide (10 ml, 0.01 mole) and the mixture is heated at 60° C. for one hour. The reaction is concentrated at reduced pressure to yield the sodium salt of 2,3-dihydro-2-oxo-1H-indole-7-acetic acid. The sodium salt is dissolved in 2:1 water:methanol and the solution is passed over a Dowex 50X-8 ion exchange resin. The eluate is concentrated at reduced pressure to yield pure 2,3-dihydro-2-oxo-1H-indole-7-acetic acid, mp 234°–236° C.

EXAMPLE 3

Preparation of 7-methylisatin

In a 5 l flask is placed chloral hydrate (90 g, 0.54 mole) and water (1200 ml). To this solution is added sodium sulfate decahydrate (1300 g, 10.9 mole) followed by a solution of o-methylaniline (54 g, 0.5 mole) in water (300 ml) containing concentrated hydrochloric acid (43 ml, 0.5 mole). Then a solution of hydroxylamine hydrochloride (110 g, 1.58 mole) in water (50 ml) is added. The reaction mixture is heated to reflux over a 90 minute period and refluxed 30 minutes. The reaction is cooled in ice and the resulting crystalline ortho-isonitrosoacetotoluidide is isolated by filtration and air dried. The ortho-isonitrosoacetotoluidide is dissolved in portions in concentrated sulfuric acid (325 ml) that is preheated to 50° C. with vigorous stirring. The reaction temperature is maintained under 75° C. When the addition is complete, the mixture is heated at 80° C. for 30 minutes, cooled, and poured unto ice (3 kg). The 7-methylisatin is isolated by filtration. The 7-methylisatin is purified by dissolution in dilute sodium hydroxide. The basic solution is treated with 4N hydrochloric acid until a slight amount of precipitation is evident. The mixture is filtered and the filtrate is acidified. The pure 7-methylisatin is recovered by filtration and dried in vacuo at 80° C. and 0.1 mm pressure, mp 270°–273° C. (A. Wahl, et al., *Ann. Chim.* 5 323 (1926); reported mp 267° C.

Preparation of 7-bromomethylisatin

The 7-methylisatin (16.1 g, 0.1 mole) is suspended in dichloroethane (2000 ml) and the suspension is heated and irradiated with a high intensity light source to the reflux point. Bromine (24.3 g, 0.15 mole) is added dropwise over a one hour period.

The solution is filtered hot and concentrated at reduced pressure to yield the product as an orange solid after washing with anhydrous diethyl ether. The product is purified using flash chromatography on silica (elution with 24:1 dichloromethane:diethyl ether) to afford after drying (at 60° C. at 0.1 mm); 7-bromomethylisatin, mp 199°–200° C. dec.

Preparation of 2,3-dihydro-2,3-dioxo-1H-indole-7-propandioic acid dimethyl ester A solution of dimethylmalonate (15.7 ml, 0.138 mole) in tetrahydrofuran is cooled to 0° C. and sodium hydride (50% in mineral oil) (6.5 g, 0.138 mole) is added portionwise over 15 minutes. The reaction is stirred at 0° C. for 30 minutes and a suspension of 7-bromomethylisatin (15.0 g, 0.0625 mole) in tetrahydrofuran (50 ml) is added in one portion. The resulting deep purple solution is stirred at room temperature for 30 minutes. 1.2N hydrochloric acid is added until the mixture turns clear yellow and the solution is concentrated at reduced pressure to 20% of the original volume. The solution is extracted with dichloromethane (2×300 ml). The combined extracts are dried (MgSO₄), filtered, and concentrated to yield a yellow solid. This is purified by flash chromatography on silica (elution with 9:1 dichloromethane:diethyl ether) to afford after concentration pure 2,3-dihydro-2,3-dioxo-1H-indole-7-propandioic acid dimethyl ester, mp 137°–140° C.

EXAMPLE 4

Preparation of 2,3-dihydro-2-oxo-1H-indole-7-propandioic acid dimethyl ester

A solution of 2,3-dihydro-2,3-dioxo-1H-indole-7-propandioic acid dimethyl ester (1.4 g, 0.0048 mole) is dissolved in acetic acid (100 ml) and in the presence of 20% Pd/C is treated with hydrogen gas at 50 psi. The solution is filtered and concentrated to yield 2,3-dihydro-2-oxo-1H-indole-7-propandioic acid dimethyl ester. This is purified by flash chromatography on silica (elution with 7:3 hexane:ethyl acetate) to give after concentration pure 2,3-dihydro-2-oxo-1H-indole-7-propandioic acid dimethyl ester, mp 161°–161.5° C.

EXAMPLE 5

Preparation of 2,3-dihydro-2-oxo-1H-indole-7-propanoic acid

A solution of 2,3-dihydro-2-oxo-1H-indole-7-propandioic acid dimethyl ester (4.6 g, 0.0166 moles) is dissolved in methanol (50 ml) and 1N sodium hydroxide (33.2 ml, 0.0332 mole) is added. The mixture is stirred at 50° C. for 90 minutes then concentrated at reduced pressure. The residue is dissolved in water (75 ml) and methanol (50 ml). The solution is made acidic with excess Dowex 50X-8 acidic ion exchange resin and heated with stirring at 70° C. for 24 hours. The solution is cooled, filtered, and concentrated to dryness to yield 2,3-dihydro-2-oxo-1H-indole-7-propanoic acid. The 2,3-dihydro-2-oxo-1H-indole-7-propanoic acid is purified by flash chromatography on silica (elution with 9:1 dichloromethane:methanol) NMR spectra: ($^1$H-CDCl₃) δ 7.30–7.10 (m, 3H), δ 6.50–6.25 (b, 1H) δ 3.80–3.70 (m, 2H), δ 3.70 (5, 2H), δ 3.28–3.22 (m, 2H).

EXAMPLE 6

Preparation of 2-nitro-1,3-benzenedimethanol

A solution of 2-nitro-1,3-benzenedicarboxylic acid (12.7 g, 0.06 mole) in tetrahydrofuran (60 ml) is cooled to 0° C. and 1N borane:tetrahydrofuran (300 ml, 0.3 mole) is added dropwise over one hour. The mixture is allowed to warm slowly to 25° C. and is stirred for 36 hours. Methanol (50 ml) is added slowly, the mixture is filtered and evaporated. The residue is dissolved in ethyl acetate (100 ml) and washed with water (25 ml), dried (MgSO₄), filtered, and evaporated to yield a yellow solid. This is further purified by flash chromatography over silica (elution with 1:1 hexane:ethyl acetate) to afford after concentration pure 2-nitro-1,3-benzenedimethanol, mp 100–101° C.

Preparation of 2-nitro-1,3-benzenediacrylic acid diethyl ester

A solution of 2-nitro-1,3-benzenedimethanol (5.0 g, 0.027 mole) in dichloromethane (90 ml) is mixed with anhydrous sodium acetate (10 g). The mixture is cooled to 0° C. and pyridinium chlorochromate (4.0 eq, 21.4 g, 0.1 mole) is added portionwise over 10 minutes. The reaction is allowed to warm to room temperature over six hours. The mixture is poured into diethyl ether (1 l) and filtered through Florosil. The colorless solution is concentrated at reduced pressure and azeotroped with heptane to remove pyridine. The resulting oil is reasonably pure 2-nitro-1,3-benzenedialdehyde and is used as is.

The 2-nitro-1,3-benzenedialdehyde (3.4 g, 0.019 mole) is dissolved in toluene (60 ml) and carbethoxymethylene triphenylphosphorane (19.2 g, 0.06 mole) is added. The mixtrre is heated at 60° C. for eight hours, cooled, and ccncentrated at reduced pressure. Diethyl ether (100 ml) is added and the mixture is filtered. The filtrate is concentrated and purified by flash chromatography over silica (elution with 4:1 hexane:ethyl acetate) to afford, after concentration, pure 2-nitro-1,3-benzenediacrylic acid diethyl ester, mp 114°–115° C.

Preparation of
1,2,3,4-Tetrahydro-2-oxo-8-quinolinepropanoic acid ethyl ester

A solution of 2-nitro-1,3-benzenediacrylic acid diethyl ester (3.5 g, 0.011 mole) in absolute ethanol (100 ml) is treated with hydrogen at 1 atmosphere pressure for 12 hours in the presence of 20% Pd/C. The mixture is filtered and concentrated at reduced pressure to yield 1,2,3,4-tetrahydro-2-oxo-8-quinolinepropanoic acid ethyl ester, mp 102°–103° C.

EXAMPLE 7

Preparation of
1,2,3,4-tetrahydro-2-oxo-8-quinolinepropanoic acid

A solution of 1,2,3,4-tetrahydro-2-oxo-8-quinolinepropanoic acid ethyl ester (2.5 g, 0.01 mole) in methanol (50 ml) is treated with 0.5N sodium hydroxide solution (19.5 ml, 0.00975 mole) and the mixture is heated at 50° C. for two hours. The mixture is concentrated at reduced pressure to yield the sodium salt of 1,2,3,4-tetrahydro-2-oxo-8-quinolinepropanoic acid· as a solid. The sodium salt of 1,2,3,4-tetrahydro-2-oxo-8-quinolinepropanoic acid is dissolved in 2:1 water:methanol (5 ml) and the solution is passed over a Dowex 50X-8 ion exchange column and the solution is concentrated at reduced pressure to yield 1,2,3,4-tetrahydro-2-oxo-8-quinolinepropanoic acid, mp 164°–165° C.

EXAMPLE 8

Preparation of
5,6-dihydro-4H-pyrrolo[3,2,1-ij]quinoline-2,4(1H)-dione

A solution of 2,3-dihydro-2-oxo-1H-indole-7-propanoic acid (2.0 g, 0.0098 mole) in acetic anhydride (8 ml) is heated to 90° C. with stirring for one hour. Excess acetic anhydride is removed at reduced pressure. The red crystalline material is purified by flash chromatography over silica (elution with 23:2 dichloromethane:diethyl ether). Final purification by fractional sublimation yields 5,6-dihydro-4H-pyrrolo[3,2,1-ij]quinoline-2,4(1H)-dione, mp 194°–197° C.

Preparation of
1,2,3,4-tetrahydro-2-oxo-8-quinolineacetic acid ethyl ester

A solution of 5,6-dihydro-4H-pyrrolo[3,2,1-ij]quinoline-2,4(1H)-dione (1.87 g, 0.01 mole) in ethanol (10 ml) is treated with a drop of concentrated hydrochloric acid. The mixture is refluxed 24 hours (or until the dione starting material can no longer be detected by thin layer chromatography). The solution is cooled and concentrated at reduced pressure. The product is purified by flash chromatography to yield 1,2,3,4-tetrahydro-2-oxo-8-quinoline acetic acid ethyl ester.

EXAMPLE 9

Preparation of
1,2,3,4-tetrahydro-2-oxo-8-quinolineacetic acid

A solution of 5,6-dihydro-4H-pyrrolo[3,2,1-ij]quinoline-2,4(1H)-dione (1.87 g, 0.01 mole) in water (10 ml) is treated with a drop of concentrated hydrochloric acid. The mixture is refluxed 24 hours (or until the starting dione can no longer be detected by thin layer chromatography). The solution is cooled, and concentrated at reduced pressure. The product is purified by flash chromatography to yield 1,2,3,4-tetrahydro-2-oxo-8-quinoline acetic acid.

EXAMPLE 10

Preparation of
1,2,6,7-tetrahydro-3H,5H-benzo[ij]quinolizine-3,5-dione 1,2,3,4-Tetrahydro-2-oxo-3-quinolinepropanoic acid (2.1 g, 0.0096 mole) is dissolved in acetic anhydride (10 ml) and the solution is heated to 100° C. for one hour. Excess acetic anhydride is removed at reduced pressure and the residual anhydride is removed by addition of toluene and repeated concentration. The solid is recrystallized from ethyl acetate to yield pure 1,2,6,7-tetrahydro-3H,5H-benzo[ij]quinolizine-3,5-dione, mp 136°–140° C.

Preparation of
1,2,3,4-tetrahydro-2-oxo-8-quinolinepropanoic acid phenylmethyl ester A solution of 1,2,6,7-tetrahydro-3H,5H-benzo[ij]quinolizine-3,5-dione (20.1 g, 0.1 mole) in phenylmethanol (200 ml) is treated with a drop of concentrated hydrochloric acid. The mixture is refluxed 24 hours (or until the starting dione can no longer be detected by thin layer chromatography). The solution is cooled and concentrated at reduced pressure. The product is purified by flash chromatography to yield 1,2,3,4-tetrahydro-2-oxo-8-quinoline propanoic acid phenylmethyl ester.

EXAMPLE 11

Preparation of
1-(4-methoxybenzoyl)-1,2,3,4-tetrahydro-2-oxo-8-quinolinepropanoic acid phenylmethyl ester A solution of 1,2,3,4-tetrahydro-2-oxo-8-quinolinepropanoic phenylmethyl ester (30.4 g, 0.1 mole) in toluene is treated with 4-methoxybenzoylchloride (17.1 g, 0.1 mole). The solution is stirred and heated to 70° C. and a solution of triethylamine (10.1 g, 0.1 mole) in toluene (100 ml) is added dropwise. Heating and stirring is continued for 18 hours. The warm mixture is filtered through filter aid and concentrated at reduced pressure. Purification by flash chromatography on silica (elution with methanol:dichloromethane, 1:19) yields 1-(4-methoxybenzoyl)-1,2,3,4-tetrahydro-2-oxo-8-quinolinepropanoic and phenylmethyl ester.

EXAMPLE 12

Preparation of 1-(4-methoxybenzoyl)-1,2,3,4-tetrahydro-2-oxo-8-quinolinepropanoic acid A solution of 1-(4-methoxybenzoyl)-1,2,3,4-tetrahydro-2-oxo-8-quinolinepropanoic acid phenylmethyl ester (10 g, 0.023 mole) is dissolved in tetrahydroferan (250 ml) and 1 g of 20% Pd/C is added. The mixture is shaken under an atmosphere of $H_2$ gas until $H_2$ absorption is complete. The mixture is filtered and concentrated at reduced pressure to yield after trituration with anhydrous diethylether and drying, 1-(4-methoxybenzoyl)-1,2,3,4-tetrahydro-2-oxo-8-quinolinepropanoic acid.

EXAMPLE 13

Preparation of 2,3-dihydro-2-oxo-1H-indole-7-acetic acid phenylmethyl ester

A solution of 20.5 g of 2,3-dihydro-2-oxo-1H-indole-7-acetic acid (0.1 mole) and 4.0 g (0.1 mole) of sodium hydroxide in 200 ml of water is vigorously stirred together with a solution of 20.5 g (0.12 mole) of benzyl bromide and 3.4 g (0.1 mole) of tetrabutylammonium bromide in 300 ml of toluene.

The mixture is heated with stirring at 85° C. for three hours. After cooling, the toluene layer is separated and the aqueous layer is extracted twice with dichloromethane (300 ml portions). The combined extracts are dried over anhydrous magnesium sulfate, filtered and concentrated at reduced pressure. Final purification of the product is accomplished using flash chromatography on silica gel (elution with 1:19 methanol:dichloromethane) to yield 2,3-dihydro-2-oxo-1H-indole-acetic acid phenylmethyl ester.

EXAMPLE 14

Preparation of 2,3-dihydro-1-(4-methoxybenzoyl)-2-oxo-1H-indole-7-acetic acid phenylmethyl ester A solution of 28.1 g (0.1 mole) 2,3-dihydro-2-oxo-1H-indole-7-acetic acid phenylmethyl ester in 400 ml of toluene is treated with 17.1 g (0.1 mole) of 4-methoxybenzoyl chloride. The mixture is heated at 70° C. with stirring and a solution of 10.2 g (0.1 mole) of triethylamine in 100 ml of toluene is added dropwise.

The mixture is stirred with heating for an additional 16 hours, filtered while warm through filter aid to remove triethylammonium hydrochloride, and concentrated at reduced pressure.

Chromatography over silica gel (elution with 1:19 methanol:dichloromethane) yields, after concentration, 2,3-dihydro-1-(4-methoxybenzoyl)-2-oxo-1H-indole-7acetic acid phenylmethyl ester.

EXAMPLE 15

Preparation of 2,3-dihydro-1-(4-methoxybenzoyl)-2-oxo-1H-indole-7-acetic acid A solution of 29.5 g (0.1 mole) 2,3-dihydro-1-(4-methoxybenzoyl)-2-oxo-1H-indole-7-acetic acid phenylmethyl ester in tetrahydrofuran is reduced with hydrogen over 2 g of 20% Pd/C catalyst. After the theoretically calculated amount of hydrogen has been consumed, the solution is filtered through filter aid. The filtrate is concentrated at reduced pressure and the oily residue is triturated with anhydrous diethyl ether to yield 2,3-dihydro-1-(4-methoxybenzoyl)-2-oxo-1H-indole-7-acetic acid.

We claim:

1. A compound having the formula

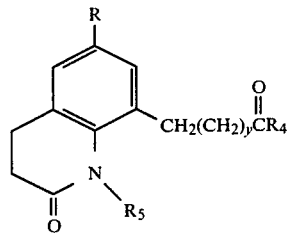

wherein y is zero or one;

R is hydrogen, halogen, hydroxyl,

—$OR_1$ where $R_1$ is alkyl of from one to six carbon atoms, phenyl, or phenylmethyl, —$NR_2R_3$ where $R_2$ and $R_3$ are independently alkyl of from one to six carbon atoms;

$R_4$ is selected from

—OH and the pharmaceutically acceptable metal, ammonium, and amine acid addition salts thereof, —$OR_1$ where $R_1$ is as previously defined,

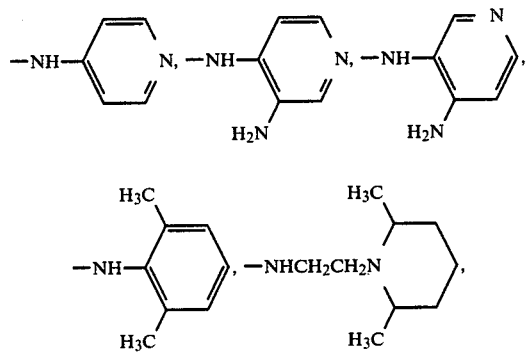

—$NHCH_2CH_2N[CH(CH_3)_2]_2$, and

—$NR_6R_7$ where $R_6$ and $R_7$ are independently hydrogen or alkyl of from one to six carbon atoms; and $R_5$ is hydrogen or

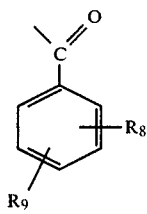

where

R₈ and R₉ are independently hydrogen, halogen, hydroxyl,

—OR₁ where R₁ is as previously defined,

—NR₁₀R₁₁ where R₁₀ and R₁₁ are independently hydrogen, alkyl of from one to six carbon atoms, or where R₈ and R₉ are attached to adjacent carbon atoms, taken together are —OCH₂O—;

with the proviso that when R₅ is hydrogen, R₄ may not be H or lower alkyl.

2. A compound in accordance with claim 1 wherein R is selected from hydrogen; fluorine; chlorine; hydroxy; —OR₁ wherein R₁ is alkyl of from one to six carbon atoms, phenyl, or phenylmethyl; or —NR₂R₃ where R₂ and R₃ are independently alkyl of from one to six carbon atoms.

3. A compound in accordance with claim 1 wherein R₄ is —OH, and the pharmaceutically acceptable salts thereof.

4. A compound in accordance with claim 1 wherein R₄ is —OR₁ wherein R₁ is alkyl of from one to six carbon atoms, phenyl, or phenylmethyl.

5. A compound in accordance with claim 1 where R₄ is

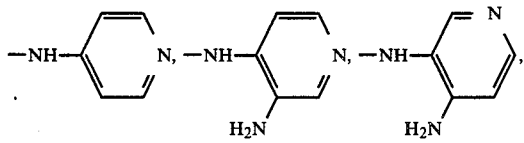

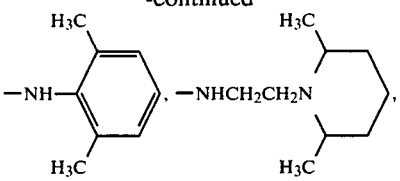

—NHCH₂CH₂N[CH(CH₃)₂]₂; or —NR₆R₇ where R₆ and R₇ are independently hydrogen or alkyl of from one to six carbon atoms.

6. A compound in accordance with claim 1 having the name 1-[4-(dimethylamino)benzoyl]-1,2,3,4-tetrahydro-2-oxo-8-quinolineacetic acid and the pharmaceutically acceptable salts thereof.

7. A compound in accordance with claim 1 having the name 1-[4-methoxy-3-(phenylmethoxy)benzoyl]-1,2,3,4-tetrahydro-2-oxo-8-quinolinepropanoic acid and the pharmaceutically acceptable salts thereof.

8. A compound in accordance with claim 1 having the name 1-(1,3-benzodioxol-5-ylcarbonyl)-1,2,3,4-tetrahydro-2-oxo-8-quinolinepropanoic acid and the pharmaceutically acceptable salts thereof.

9. A compound in accordance with claim 1 having the name 1-(4-methoxybenzoyl)-1,2,3,4-tetrahydro-2-oxo-8-quinolineacetic acid and the pharmaceutically acceptable salts thereof.

10. A compound in accordance with claim 1 having the name 1,2,3,4-tetrahydro-2-oxo-8-quinolineacetic acid phenylmethyl ester.

11. A compound in accordance with claim 1 having the name 1,2,3,4-tetrahydro-2-oxo-8-quinolinepropanoic acid phenylmethyl ester.

12. A compound in accordance with claim 1 having the name 1-(2-fluorobenzoyl)-6-methoxy-1,2,3,4-tetrahydro-2-oxo-8-quinolineacetic acid phenyl ester.

13. A compound in accordance with claim 1 having the name 1-(2-methoxybenzoyl)-1,2,3,4-tetrahydro-2-oxo-6-phenoxy-8-quinolinepropanoic acid and the pharmaceutically acceptable salts thereof.

14. A compound in accordance with claim 1 having the name 1-(2-methoxybenzoyl)-1,2,3,4-tetrahydro-2-oxo-6-phenoxy-8-quinolinepropanoic acid phenylmethyl ester.

15. A pharmaceutical composition useful for reversing the effects of electroconvulsive shock-induced amnesia in a mammal comprising an effective amount of a compound in accordance with claim 1 in combination with a pharmaceutically acceptable carrier.

16. A method of reversing electroconvulsive shock-induced amnesia in mammals comprising administering to said mammal an effective amount of of a pharmaceutical composition in accordance with claim 15.

* * * * *